United States Patent [19]
Ratcliffe et al.

[11] Patent Number: 4,668,825
[45] Date of Patent: * May 26, 1987

[54] PRODUCTION OF METHANETHIOL FROM $H_2S$ AND CO

[75] Inventors: Charles T. Ratcliffe, Pittstown, N.J.; Petrus J. Tromp, Amsterdam, Netherlands

[73] Assignee: Exxon Research and Engineering Co., Florham Park, N.J.

[ * ] Notice: The portion of the term of this patent subsequent to May 14, 2002 has been disclaimed.

[21] Appl. No.: 625,957

[22] Filed: Jun. 29, 1984

[51] Int. Cl.$^4$ .................... C07C 149/06; C07C 149/10
[52] U.S. Cl. ................................. 568/70; 423/648 R; 568/60; 585/733
[58] Field of Search ............... 568/60, 70; 423/648 R; 585/733

[56] References Cited

U.S. PATENT DOCUMENTS

| | | | |
|---|---|---|---|
| 3,856,925 | 12/1974 | Kodera et al. | 423/416 |
| 3,963,785 | 6/1976 | Kubicek | 260/609 B |
| 4,369,108 | 1/1983 | Bertolacini et al. | 208/120 |
| 4,410,731 | 10/1983 | Buchholz | 568/70 |
| 4,449,006 | 5/1984 | Haines | 568/70 |
| 4,517,171 | 5/1985 | Ratcliffe et al. | 423/648 R |
| 4,570,020 | 2/1986 | Ratcliffe et al. | 568/60 |

OTHER PUBLICATIONS

Y. Onishi et al, Bull. Chem. Soc. Japan, vol. 43, 996–1000 (1970), The Catalytic Oxidation of Carbon Monoxide or Titanium Dioxide; Anatase and Rutile.

*Primary Examiner*—Donald G. Daus
*Assistant Examiner*—Mary E. Ceperley
*Attorney, Agent, or Firm*—Edward M. Corcoran

[57] ABSTRACT

Methanethiol is produced from a gaseous feed comprising a mixture of $H_2S$ and CO by contacting said feed with a catalyst comprising rutile titania at a temperature of at least about 225° C.

21 Claims, 1 Drawing Figure

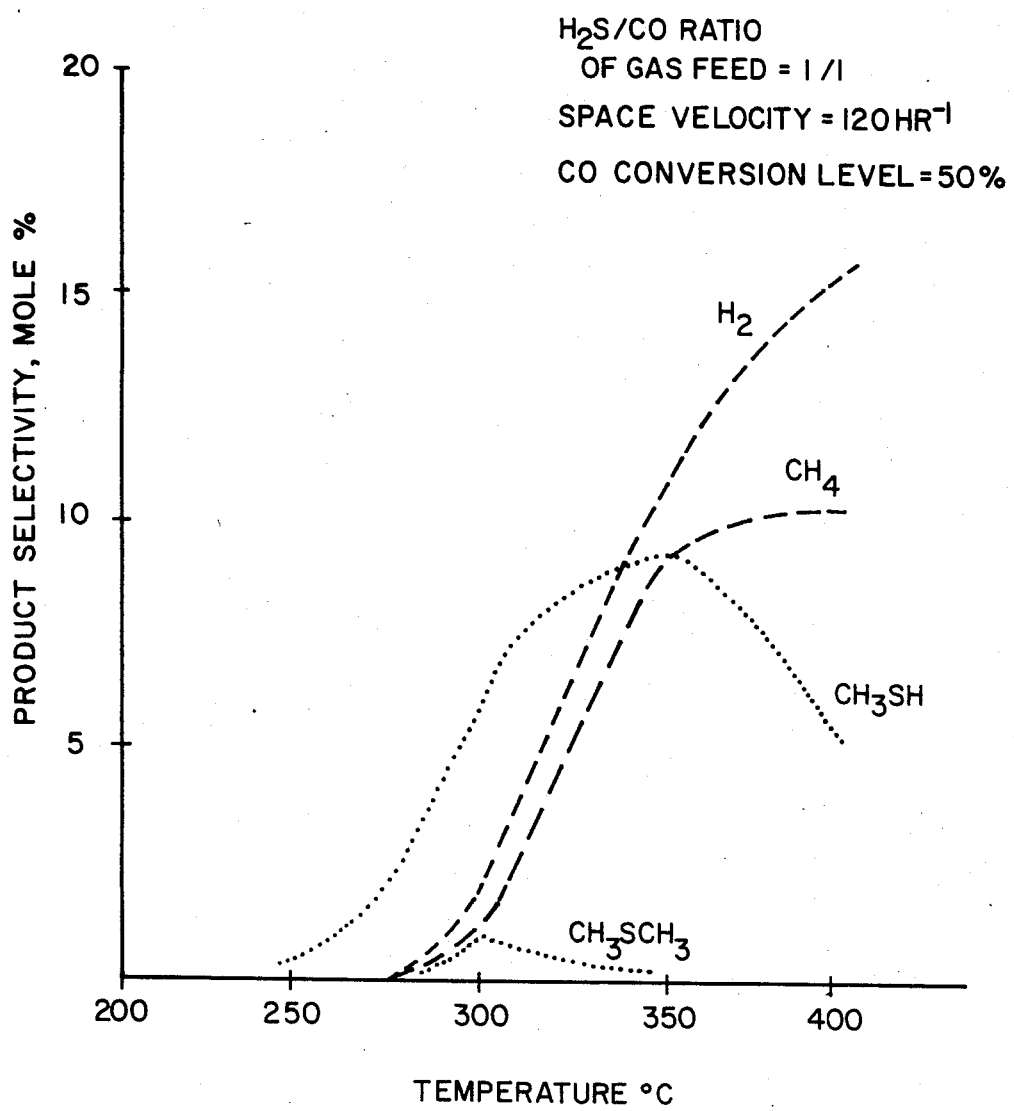

PRODUCTION OF METHANETHIOL FROM H₂S AND CO

BACKGROUND OF THE INVENTION

1. Field of the Invention

This invention relates to producing methanethiol from $H_2S$ and CO. More particularly, this invention relates to producing methanethiol by passing a gas feed comprising a mixture of $H_2S$ and CO over a catalyst comprising rutile titania at a temperature of at least about 225° C. for a time sufficient to convert at least a portion of said feed to methanethiol.

2. Background of the Disclosure

Hydrogen sulfide is an unwanted by-product of many refinery processes, being very toxic and having few practical uses. In many cases, $H_2S$ is disposed of by the Claus Process in which a portion of the $H_2S$ is oxidized to $SO_2$. The remaining $H_2S$ is then reacted with the $SO_2$ in the presence of a suitable catalyst to produce $H_2O$ and elemental sulfur. $H_2S$ can also be reacted with oxygen in the presence of an iron oxide catalyst to form water and elemental sulfur.

Some uses of $H_2S$ include conversion of mononitro aromatic compounds to amino compounds as disclosed in U.S. Pat. No. 4,326,081. In U.S. Pat. No. 4,235,699, Ratcliffe, et al. disclose forming lower molecular weight products from coal and coal tar using a mixture of CO and $H_2S$ as a hydrogenating agent. Fukuda, et al. in "Catalytic Activity of Metal Sulfides for the Reaction, $H_2S + CO = H_2 + COS$", J. Catalysis 49, p. 379–382 (1977), studied first row transition metal sulfides as catalysts for producing COS and $H_2$ from mixtures of $H_2S$ and CO (see also Masayuki, et al., "The Study of Thermochemical Hydrogen Preparation. VI. A Hydrogen-evolving Step Through the $H_2S$—CO Cycle", Bull. Chem. Soc. Japan, 51 (1) p. 150–153 [1978]).

More recently, Happel, et al. in U.S. Pat No. 4,151,191 have disclosed the use of sulfur resistant catalysts for methane production in the presence of $H_2S$. This reference discloses producing methane from a feed mixture containing $H_2$, CO and gaseous sulfur compounds, such as $H_2S$, by contacting the feed with a predominantly molybdenum oxide catalyst containing at least one element of lanthanide or actenide groups of elements at a temperature of about at least 300° C. U.S. Pat. No. 3,963,785 discloses the synthesis of aliphatic thiols by reacting $H_2S$ with olefins or aldehydes in the presence of $CS_2$. Finally, Kodera, et al. in U.S. Pat No. 3,856,925 disclose the manufacture of $H_2$ and COS from mixtures of $H_2S$ and CO using various Group VB, VIB and VIII metal sulfides as catalysts.

SUMMARY OF THE INVENTION

The present invention relates to producing methanethiol, $CH_3SH$, from a gaseous feed comprising a mixture of $H_2S$ and CO by contacting said feed, at a temperature of at least about 225° C., with a catalyst comprising rutile titania for a time sufficient to convert at least a portion of said CO and $H_2S$ to methanethiol. Those skilled in the art know that methanethiol, $CH_3SH$, is also known as methyl mercaptan. Rutile titania is meant to include mixtures of rutile with other forms of titania, such as anatase, as well as substantially pure rutile. The greater the rutile content of the titania, the greater will be the amount of feed converted to the desired $CH_3SH$ product.

The rutile titania catalyst must be sulfided for the process of this invention. This sulfiding may be accomplished in-situ in a reactor or the catalyst may be presulfided. Any suitable sulfur containing compound known to those skilled in the art as useful for sulfiding catalysts may be used. Illustrative, but non-limiting examples include $H_2S$, $CS_2$, various thiols, etc. In one embodiment the catalyst will be sulfided in-situ by contact with the $H_2S$/CO feed at elevated temperature.

In general, the methanethiol may be produced according to the process of this invention over a temperature range of from about 225°–400° C. However, those skilled in the art know that methanethiol is thermally unstable and decomposes at temperatures above about 300° C. Hence, if the reaction is run at a temperature above about 300° C. it will be necessary to quench the methanethiol product to a temperature below 300° C. in order to avoid its decomposition to methyl sulfide, $(CH_3)_2S$, and/or other products.

BRIEF DESCRIPTION OF THE DRAWING

The FIGURE is a graph illustrating mole % product selectivity as a function of reaction temperature of products formed by reacting a mixture of $H_2S$ and CO in the presence of a catalyst comprising rutile titania.

DETAILED DESCRIPTION

Those skilled in the art know that methanethiol or methyl mercaptan is used as an odorant or tracer for natural gas and is also used as a raw material in the manufacture of methionine, fungicides and jet fuel additives.

As stated above, the present invention relates to producing methanethiol from a gaseous feed comprising a mixture of $H_2S$ and CO by contacting said feed with a catalyst comprising rutile titania at a temperature of at least about 225° C. As a practical matter, a minor amount of methyl sulfide, $(CH_3)_2S$, will also be produced by the process of this invention as can be seen from the FIGURE. The amount of methyl sulfide produced by this process depends on the reaction conditions employed and increases with increasing reaction temperature and decreasing space velocity of the gaseous feed in the reaction zone.

As previously stated, the process of this invention will occur at an elevated temperature of at least about 225° C. Referring to the FIGURE, one can readily see that the onset of methaethiol production starts to occur at a temperature of about 225° C., and more preferably about 250° C., and reaches a peak (under the particular reaction conditions and feed mixture set forth in the FIGURE) or optimum at a temperature of about 350° C. However, as previously stated, methanethiol is thermally unstable at 350° C. Therefore, if the reaction temperature approaches and/or exceeds this temperature, one must take provisions to rapidly quench the so-formed methanethiol down to a temperature below about 350° C. in order to prevent thermal decomposition thereof.

Referring again to the FIGURE, one can see that hydrogen and methane are also produced as a result of reacting a gaseous feed comprising a mixture of CO and $H_2S$ in the presence of rutile titania catalyst. However, one can also see that a different temperature regime applies to the production of methane and hydrogen. To produce predominantly methane and hydrogen, one would preferably conduct the reaction at a temperature above about 350° C. and even more preferably above about 400° C.

Most commercially available titanias in a form suitable for use as a catalyst comprise mixtures of anatase and rutile titania. It has been found and forms a part of this disclosure that the anatase form titania does not effectively act as a catalyst for the process of this invention, but that the rutile form of titania does. It has also been found that the greater the rutile content of a mixed rutile/anatase catalyst, the greater will be the amount of feed converted, with maximum conversion occurring using all rutile titania as the catalyst, assuming equal surface area. Laboratory studies on specially prepared catalyst samples which factored out surface area differences have shown that specific conversion of the $H_2S$ in the feed, expressed as moles of $H_2S$ converted per gram of catalyst per $m^2$ of catalyst surface area, steadily increases with increasing rutile content of catalysts consisting of mixtures of anatase titania and rutile titania. Thus, the term "rutile titania" as used in the context of this invention is not meant to be restricted to a catalyst consisting of rutile titania but includes catalysts comprising mixtures of anatase and rutile titania as well as rutile titania and mixtures of anatase and rutile titania mixed with other suitable inorganic refractory oxide materials which will act merely as diluents and which will not adversely affect the process.

In general, the ratio of $H_2S$ to CO in the gaseous feed used in the process of this invention will typically range from about ¼ to 40/1 and more preferably from about ½ to 4/1 on a mole basis. It has been found experimentally that a 1/1 ratio appears to be the optimum for maximum conversion of the feed. The reaction temperature will generally range from about 225° to 450° C., preferably 250° to 400° C. and still more preferably from about 300° to 400° C. However, as previously stated, exceeding a reaction temperature of 350° C. may necessitate a quenching of the $CH_3SH$ product in order to avoid its thermal decomposition. With regard to the space velocity of the feed, it is understood that longer contact times will result in a greater amount of product. However, this may be offset by decomposition of $CH_3SH$ product in contact with the catalyst. In general, the space velocity will be maintained below about 4800 V/V/hr.

Because the process of this reaction is a gas phase reaction, the partial pressure of the $H_2S$ is limited to a maximum of approximately 260 psig, which is the pressure at which $H_2S$ liquifies. Accordingly, one will not want to exceed a partial pressure of 260 psig for the $H_2S$ in the feed gas unless it is desired that the reaction occur in the presence of both gaseous and liquid phases.

It has also been found that the rutile titania catalyst useful in the process of this invention has relatively little activity if it is put on stream without being presulfided. However, the catalyst may, if desired, be sulfided in-situ. Thus, an unsulfided rutile titania catalyst may be charged into a reactor and contacted with an $H_2S$/CO feed stream at elevated temperature. Initially, the catalyst will exhibit little activity. However, as time progresses and the reaction proceeds, the activity of the catalyst will continuously increase up to a point and then level out.

The invention will be more readily understood by reference to the examples.

EXAMPLES

EXPERIMENTAL

Hydrogen sulfide was obtained in compressed cylinders from Scientific Gas Products (electronic grade 99.999% purity), while carbon monixide was purchased from Matheson Gas (99.99% purity). The above gases were checked for absence of hydrocarbon impurities (MS analysis and G.C. analysis with FID detector) and used without further purification. Helium (99.99%), when used as an inert carrier gas, was predried in a molecular sieve trap, scrubbed for $O_2$ removal in a hot Cu trap, and redried in a molecular sieve trap.

Gas flows were regulated with Tylan F-260 flow controllers and premixed in a gas manifold system prior to entering into the catalyst bed. A quartz reactor tube of 9 mm ID by 700 mm was loaded with 2.5 gram samples of −40/+60 mesh (Tyler) catalyst particles which were supported on each end with degreased quartz wool plugs. An external thermocouple was attached to the outside of the quartz tube near the center of the catalyst bed to record reaction temperature. The tube was heated with a three zone electric furnace (ATS-3210) equipped with Omega set point controllers.

Product analysis was accomplished with an on-line Carle GC (series Sx) equipped with a hydrogen transfer system and FID/TC detectors. Gas phase samples were also separated on a Perkin Elmer 900 GC coupled to a DuPont 21–491 mass spectrometer for product identification and analysis of $CH_3SH$ and $CH_3SCH_3$. Response factors for quantitative G.C. analysis were obtained from a primary standard mixture of gases with quantities similar to the product mixture.

The catalysts were made from three different sources of titania. DeGussa P-25 titania powder was obtained and moistened with acetone, pressed into tablets, heated to 575° C. for 12 hours, and then ground and meshed to −40/+60 (Tyler) prior to use. Comparative examples of DeGussa P-25 with higher rutile titania contents were prepared by heating the P-25 pellets in air at 800° C. for periods of time of from 2–8 hours in order to achieve the desired rutile content or rutile/anatase ratio. Harshaw $TiO_2$-0720 pellets were ground to the desired mesh size followed by heating to 600° C. in air for 24 hours to burn off the carbon binder in the pellets. A high anatase content titania was obtained from Mobay Co. and was used after drying at 575° C. Surface areas of the catalyst samples were obtained by standard BET measurements. The relative anatase and rutile contents of the titania catalysts were measured from their respective X-ray powder pattern peaks at (20) 25.3° and 27.4°, respectively.

EXAMPLE 1

This experiment demonstrates the effect of rutile content of the titania catalyst on $H_2S$ and CO conversion as a function of temperature. In this experiment each sample of Degussa P-25 catalyst was charged to the reactor which was then heated up to a temperature of 200° C. in flowing helium. After the reactor achieved a temperature of 200° C., a 1/1 molar mixture of $H_2S$/CO was introduced to the reactor. The reactor was then held at isothermal conditions in order to establish steady-state conditions with respect to feed conversion and product selectivity. The temperature was then raised at 50° C. intervals and held at each temperature for one hour to measure activity and selectivity. After the reaction had progressed for an hour at 400° C. the temperature was slowly reduced back to 300° C. and held there for an hour after which the CO and H₂S conversion were measured. This procedure was used to determine changes in conversion or selectivity.

The results are shown in Table 1 and clearly show that it is the rutile and not the anatase form of the titania which catalyzes the $H_2S$ conversion, and that the essentially pure anatase sample exhibited no measurable catalytic activity for the $H_2S$ or CO conversion. It should be noted that less than 0.5 percent is the minimum detection level of CO in diluted gas streams with thermal conductivity detectors. Thus, it is not known if any CO or $H_2S$ was converted over the pure anatase catalyst. Further, inspection of the data in Table 1 indicates that the activity of the catalyst increased with increasing exposure to the feed mixture as evidenced by the higher activity going back down to 300° C. and the 300° C. activity exhibited with a fresh sample of catalyst. This thus indicates that exposure to the feed has an effect of treating or sulfiding the catalyst in-situ to obtain a more active species whose identity is not known. Thus, the catalyst may be pretreated or may be treated in-situ in the reaction zone.

EXAMPLE 2

This experiment was similar to that of Example 1 except that the effect of pretreatment of the catalyst was studied. The catalyst used was a DeGussa P-25 having a surface area of 39 m²/g and a 47 percent rutile content. In this experiment the catalyst was pretreated with either $H_2S$, CO or air for a time and temperature shown in Table 2 before being contacted with the 1/1 molar $H_2S$/CO feed stream. The results are contained in Table 2 and show that pretreatment with $H_2S$ enhances the activity of the catalyst, but that increased catalyst activity is also achieved if the catalyst is treated in-situ with the $H_2S$/CO feed stream.

EXAMPLE 3

This experiment was similar to that of Example 1, except that three different catalysts were used, each with a different rutile content and surface area. The results of this experiment are shown in Table 3. Comparing the results of this experiment with those of Example 1 in Table 1, one can see that greater surface area results in increased catalyst activity provided that the catalyst has some rutile content. However, comparing the 5% rutile catalyst in Table 1 with the 98% rutile catalyst of this experiment, shows that even though the 5% rutile catalyst had an extremely high surface area, it was not as effective for $H_2S$ conversion as the 98% rutile catalyst having one-tenth of the surface area.

EXAMPLE 4

In this experiment a catalyst bed of a sample of the DeGussa P-25 titania used in Example 2 was presulfided at 450° C. for two hours and forty-five minutes using a mixture of 2 ml/min $H_2S$ and 2 ml/min CO and then cooled to 200° C. with flowing helium. A gas feed comprising a mixture of 2.03 cc/min. of $H_2S$ and 1.95 cc/min. of CO was then introduced into the reactor and the temperature increased at 50° C. increments as outlined in Example 1. The results are shown in the FIGURE.

TABLE 1

Activity of Anatase Versus Rutile Titania

| | Mobay | DeGussa P25 1 hour in air at 800° C. | DeGussa P25 Overnight in air at 800° C. |
|---|---|---|---|
| % Rutile | 0% | 98% | 100% |
| Surface area[a] | 8.3 m²g | 13 m²/g | 5 m²/g |
| CO Conversion (mole %) | | | |
| 300° C.[b] | <0.5 | 8 | 3.5 |
| 350° C. | 2 | 29 | 10 |
| 400° C. | 4 | 32 | 12 |
| 300° C.[c] | <0.5 | 15 | 3 |
| H₂S Conversion (%) | | | |
| 300° C.[b] | <0.5 | 3 | 1 |
| 350° C. | 1 | 16 | 7 |
| 400° C. | 2.5 | 20 | 9 |
| 300° C.[c] | <0.5 | 7 | 1.5 |

Notes: [a]BET
[b]350° C., 400° C. analysis at increasing temperature plateaus
[c]300° C. on decreasing temperature plateau.

TABLE #2

Effect of Pretreatment on Initial Conversion

| Catalyst Weight Pretreatment (Time) | 2.5 g None | 2.5 g H₂S at 450° C. (2 hours) | 2.5 g CO at 450° C. (3 hours) | 2.5 g air at 550° C. (24 hours) |
|---|---|---|---|---|
| CO Conversion (%) | | | | |
| 300° C.[a] | 5.5% | 23 | 13 | 5 |
| 350° C. | 47% | 49 | 43 | 48 |
| 400° C. | 45% | 49 | 48 | 49 |
| 300° C.[b] | 23% | 23 | 23 | 22 |
| H₂S Conversion (%) | | | | |
| 300° C.[a] | 2% | 8.5 | 4.5 | 2 |
| 350° C. | 18.5% | 20 | 17 | 19 |
| 400° C. | 19% | 21.5 | 21.5 | 22.5 |
| 300° C.[b] | 9% | 8.5 | 9 | 8.5 |

Notes:
[a]350° C., 400° C. analysis at increasing temperature plateaus
[b]300° C. on decreasing temperature plateau.

TABLE #3

H₂S and CO Conversion vs. Temperature

| | DeGussa P25 | Harshaw Ti 0720 | Mobay |
|---|---|---|---|
| Surface area[d] | 39 m²/g | 148 m²/g | 8.3 m²/g |
| % Rutile | 47% | 5% | 0% |
| Catalyst Weight | 2.5 g | 2.5 g | 2.5 g |
| CO Conversion (mole %)[a] | | | |
| 300° C.[b] | 5.5 | 7. | <0.5 |
| 350° C. | 47 | 17.5 | 2 |
| 400° C. | 45 | 25.5 | 4 |
| 300° C.[c] | 23 | N.A. | <0.5 |
| H₂S Conversion (mole %)[a] | | | |
| 300° C.[b] | 2 | 1 | <0.5 |
| 350° C. | 18.5 | 5.5 | 1 |
| 400° C. | 19 | 11 | 2.5 |
| 300° C.[c] | 9 | N.A. | <0.5 |

Notes:
[a]300° C.
[b]350° C., 400° C. analysis at increasing temperature plateaus;
[c]300° C. on decreasing temperature plateau.
[d]BET

What is claimed is:
1. A process for producing methanethiol from a gaseous feed comprising a mixture of CO and $H_2S$, said process comprising contacting said feed, at a temperature of at least about 225° C., with a catalyst comprising rutile titania for a time sufficient to convert at least a portion of said feed to methanethiol.

2. The process of claim 1 wherein said reaction temperature ranges between from about 225°–450° C.

3. The process of claim 2 wherein the ratio of $H_2S$ to CO in said gaseous feed ranges between about 1/4 to 40/1 on a mole basis.

4. The process of claim 3 wherein said reaction temperature ranges between about 225°–400° C.

5. The process of claim 4 wherein said ratio of $H_2S$ to CO in said gaseous feed ranges between about 1/2 to 4/1.

6. The process of claim 5 wherein said reaction temperature ranges between about 300° to 400° C.

7. The process of either of claims 1, 3 or 6 wherein said reaction product is quenched below a temperature of about 350° C. to avoid the decomposition thereof.

8. A process for producing methanethiol from a gaseous feed comprising a mixture of CO and $H_2S$, said process comprising contacting said feed at a temperature of at least about 225° C. with a catalyst comprising rutile titania for a time sufficient to convert at least a portion of said $H_2S$ nd CO to methanethiol, wherein said conversion reaction occurs with the $H_2S$ in the gaseous phase.

9. The process of claim 8 wherein said reaction pressure is below about 226 psig.

10. The process of claim 9 wherein said reaction temperature ranges between from about 225°–450° C.

11. The process of claim 10 wherein the ratio of $H_2S$ to CO in said gaseous feed ranges between about 1/4 to 40/1 on a mole basis.

12. The process of claim 11 wherein said reaction temperature ranges between about 225°–400° C.

13. The process of claim 12 wherein said ratio of $H_2S$ to CO in said gaseous feed ranges between about 1/2 to 4/1.

14. The process of claim 13 wherein said reaction temperature ranges between about 300° to 400° C.

15. The process of either of claims 8, 11 or 13 wherein said reaction product is quenched below a temperature of about 350° C. to avoid the decomposition thereof.

16. A process for producing methanethiol from a gaseous feed comprising a mixture of CO and $H_2S$, said process contacting said feed at a temperature of at least about 225° C. with a catalyst comprising a sulfided rutile titania for a time sufficient to convert at least a portion of said CO and $H_2S$ to methanethiol, wherein said conversion reaction occurs at a pressure below about 226 psig to ensure that the $H_2S$ remains in the gaseous phase in the reaction zone.

17. The process of claim 16 wherein the ratio of $H_2S$ to CO in said gaseous feed ranges between about 1/4 to 40/1 on a mole basis.

18. The process of claim 17 wherein said reaction temperature ranges between about 225° to 400° C.

19. The process of claim 18 wherein said ratio of $H_2S$ to CO in said gaseous feed ranges between about 1/2 to 4/1.

20. The process of claim 19 wherein said reaction temperature ranges between about 300° to 400° C.

21. The process of either of claims 16, 17 or 19 wherein said reaction product is quenched below a temperature of about 350° C. to avoid the decomposition thereof.

* * * * *